United States Patent [19]

Ishikawa et al.

[11] 4,135,088
[45] Jan. 16, 1979

[54] CHARGED-PARTICLE ANALYZER

[75] Inventors: Isao Ishikawa, Hino; Michiyasu Itoh, Iruma; Katsuhisa Usami, Tokyo, all of Japan

[73] Assignee: Hitachi, Ltd., Japan

[21] Appl. No.: 810,970

[22] Filed: Jun. 28, 1977

[30] Foreign Application Priority Data

Jun. 28, 1976 [JP] Japan .................................. 51-75559

[51] Int. Cl.$^2$ ...................... H01J 39/00; G01M 23/00
[52] U.S. Cl. ..................................... 250/307; 250/305; 250/310
[58] Field of Search ................ 250/281, 307, 305, 310

[56] References Cited
U.S. PATENT DOCUMENTS 3,691,341  9/1972  Roiron ............................ 250/305
3,742,214  6/1973  Helmer et al. .................... 250/305
3,942,012  3/1976  Boux ............................... 250/305

Primary Examiner—Harold A. Dixon
Attorney, Agent, or Firm—Craig & Antonelli

[57] ABSTRACT

A charged-particle beam correction arrangement for a charged-particle analyzer having deflecting electrodes which focus charged particles emitted from a sample onto a center axis, an extension thereof, or onto an identical circumference with its center on the axis, a slit which is disposed at the focus point, and an energy analyzer whose object point lies at the focus point. The charged-particle beam correction arrangement is disposed axially symmetrically in the vicinity of the path of the charged particles between the sample and the slit to correct a deformation in the focusing of the charged-particle beam.

6 Claims, 5 Drawing Figures

CHARGED-PARTICLE ANALYZER

BACKGROUND OF THE INVENTION

The present invention relates to a charged-particle analyzer.

For the analysis of a feeble electron beam of low energy, such as Auger electrons and photoelectrons in the surface analysis, it is important to efficiently utilize the electrons emitted from a sample. Accordingly, it is necessary that the accepted solid angle (= the solid angle of electron rays entering an analyzing system/the entire solid angle of electron rays emitted from a sample) be wide.

As an optimum structure based on such requirement, an analyzing equipment shown in FIG. 1 has been proposed (Japanese Patent Application No. 12283/76). The feature of this equipment is that a deflecting system consisting of two inner and outer electrodes is arranged axially symmetrically around a sample and that signals emitted from the sample and entering the deflecting system are caused to depict a greatly curved track, whereupon they are focused on the center axis of the equipment or a circumference with its center on the axis again. Further, at a stage succeeding the deflecting system, an analyzing system is arranged in such electro-optical relation that the point of the above focusing is considered as the emission point of the signals. Thus, an energy analysis of photo-electrons, Auger electrons, etc. is carried out.

FIG. 1 is a constructional view showing the prior art equipment described above including an electron gun. An electron beam 2 produced from the electron gun is focused by a focusing lens 3, and irradiates a sample 4. Charged particles 5, such as Auger electrons, are emitted from the irradiated point P of the sample 4 in substantially the COS-Law spacial distribution. Among the charged particles, rays of electrons are surrounded by two cones whose vertexes are the point P and whose half vertical angles are $\theta + a$ and $\theta - a$, which rays enter between deflecting electrodes 6 and 7. The deflecting electrodes 6 and 7 are disposed axially symmetrically and are L-shaped in section so as to form a double electrode system.

Within the deflecting electrode system, the rays of electrons depict greatly curved tracks owing to a deflecting electric field. Further, the rays of electrons have the tracks corrected by an auxiliary electrode 8 and are converged in the first order of the angle a onto a slit 9 situated at a stage succeeding the auxiliary electrode 8. After passing through the slit 9, the rays travel so as to cross on the axis of the equipment. They are subjected then to the energy analysis by a cylindrical mirror type analyzer 10 arranged after the slit 9 with only electrons having certain specific energy being converged onto a detection slit 9' which is placed on the axis, signals being detected by a detector 11 which is disposed behind the detecting slit 9'.

The energy analysis of the charged particles 5 emitted from the sample becomes possible in such a way that voltages to be applied to the deflecting electrodes 6, 7, the auxiliary electrode 8, and the electrode of the cylindrical mirror type analyzer 10 are appropriately selected with divider resistances 12, 13 and 14 connected to a power source 20 and then scanned at a fixed ratio.

When it is desired to have a high sensitivity of analysis utilizing the aforedescribed analyzing system, the signal obtained from the sample must of course be received at the widest possible accepted solid angle as stated above. Additionally, the loss of signal between the deflecting system and the slit must be confined to a minimum. To this end, it is necessary that the rays of electrons at the time when they pass through the slit 9 have the best possible circularity so as to reduce the amount to which the rays are intercepted by the end face of the slit 9.

In this respect, a glass plate coated with a phosphor was placed at the position of the slit 9 in the aforedescribed equipment, and the shape of the rays of electrons focused on this point was directly observed. It was determined that the rays of electrons were not truly circular, but rather often presented a ring shape deformed in one direction or a shape having a long tail at a certain part.

The cause therefor was studied, and has been revealed to be a kind of electrooptical astigmatism attributed to the fact that the electrodes were not fixed coaxially or that the parallelism of each electrode was not maintained. Therefore, in constructing the equipment, careful attention was pair to the finish precision of the electrodes and the assembling was carefully executed. While considerable improvements were thus effected, it has been determined that a satisfactory result has not been attained.

SUMMARY OF THE INVENTION

An object of the present invention is to provide an improved charged-particle analyzer.

Another object of the present invention is to provide a charged-particle analyzer which makes it possible to set a wide accepted solid angle for signals and to attach a sample of large area without greatly decreasing the accepted solid angle.

These and other objects are attained by a charged-particle analyzer having an irradiation device for irradiating a sample with a primary beam, a deflecting electrode system for focusing charged particles emitted from the sample onto the center axis of the primary beam or an extension thereof or onto an identical circumference with its center located on the axis or the extension, a slit which is disposed at the focus point of the charged particles, an energy analyzing system whose object point lies at the focus point, a detector for detecting the charged particles analyzed by the energy analyzing system, and a charged-particle beam correction arrangement disposed axially symmetrically in the vicinity of the path of the charged particles between the sample and the slit.

BRIEF DESCRIPTION OF THE DRAWINGS

FIG. 3A is a schematic plan view showing the construction of charged-particle beam correction arrangement according to the present invention, while

DETAILED DESCRIPTION OF THE PREFERRED EMBODIMENTS

In accordance with the present invention, there is provided, in a charged-particle analyzer, a charged-particle beam correction arrangement in the vicinity of the path of charged particles between a sample and a slit which is disposed at the object point of an energy analyzing system, for example, cylindrical mirror type analyzer.

By employing such a charged-particle beam correction arrangement, there is provided a compensation for the deformation of a charged-particle beam, which deformation has heretofore not been eliminated even by enhancing the mechanical precision of deflecting electrodes, etc.

Figure 2:
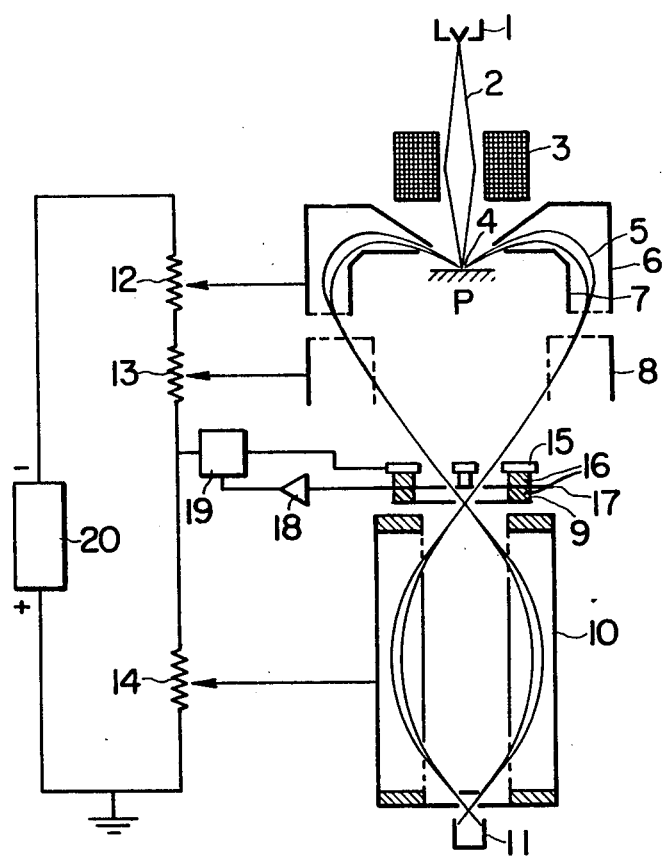
FIG. 2 schematically illustrates a charged-particle analyzer according to the present invention.
Figure 3A:
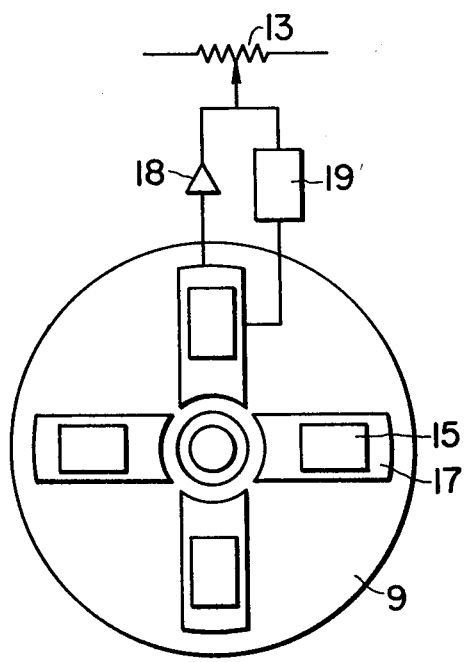
Figure 3B:
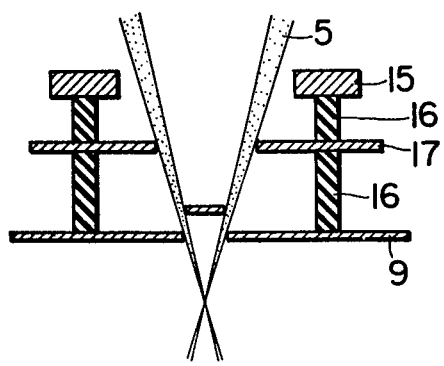
FIG. 3B is a partial sectional view for explaining the operation of the charged-particle beam correction arrangement of the present invention.

The present invention will now be described in connection with the following figures wherein FIG. 2 shows an embodiment of an electrostatic charged-particle analyzer on which the charged-particle beam correction arrangement of the present invention is installed and FIGS. 3A and 3B show the details of the charged-particle beam correction arrangement.

The charged-particle beam correction arrangement includes a detection electrode 17 for detecting the charged-particle beam and a correction electrode 15 fixed on the slit 9 through insulators 16, as shown in FIG. 3B. A plurality of detection and correction electrodes are arranged axially symmetrically. Therefore, end portion of the detection electrode 17 and the slit 9 are positionally related so as not to intercept the charged-particle beam which enters the slit 9.

The correction of the shape of the charged-particle beam is achieved in the manner described below. A state of the charged-particle beam which deviates slightly from the optimum condition for the entrance of the charged-particle beam into the slit 9 is established so that part of the charged-particle beam impinges on the detection electrodes 17. Thus, the quantities of the charged particles flowing into the detection electrodes can be measured.

If the quantities of the charged particles flowing into the respective detection electrodes 17 are equal, it follows that the shape of the charged-particle beam entering the slit 9 is concentrically circular. However, if the quantities of the charged particles entering the respective detection electrodes are different, voltages to be applied to the correction electrodes 15 are adjusted by an amplifier 18 and a variable power source 19 so as to adjust electric fields to act on the charged-particle beam. In this manner, the shape of the charged-particle beam is corrected to form a charged-particle beam of high circularity, which is caused to enter the slit 9.

Figure 4:
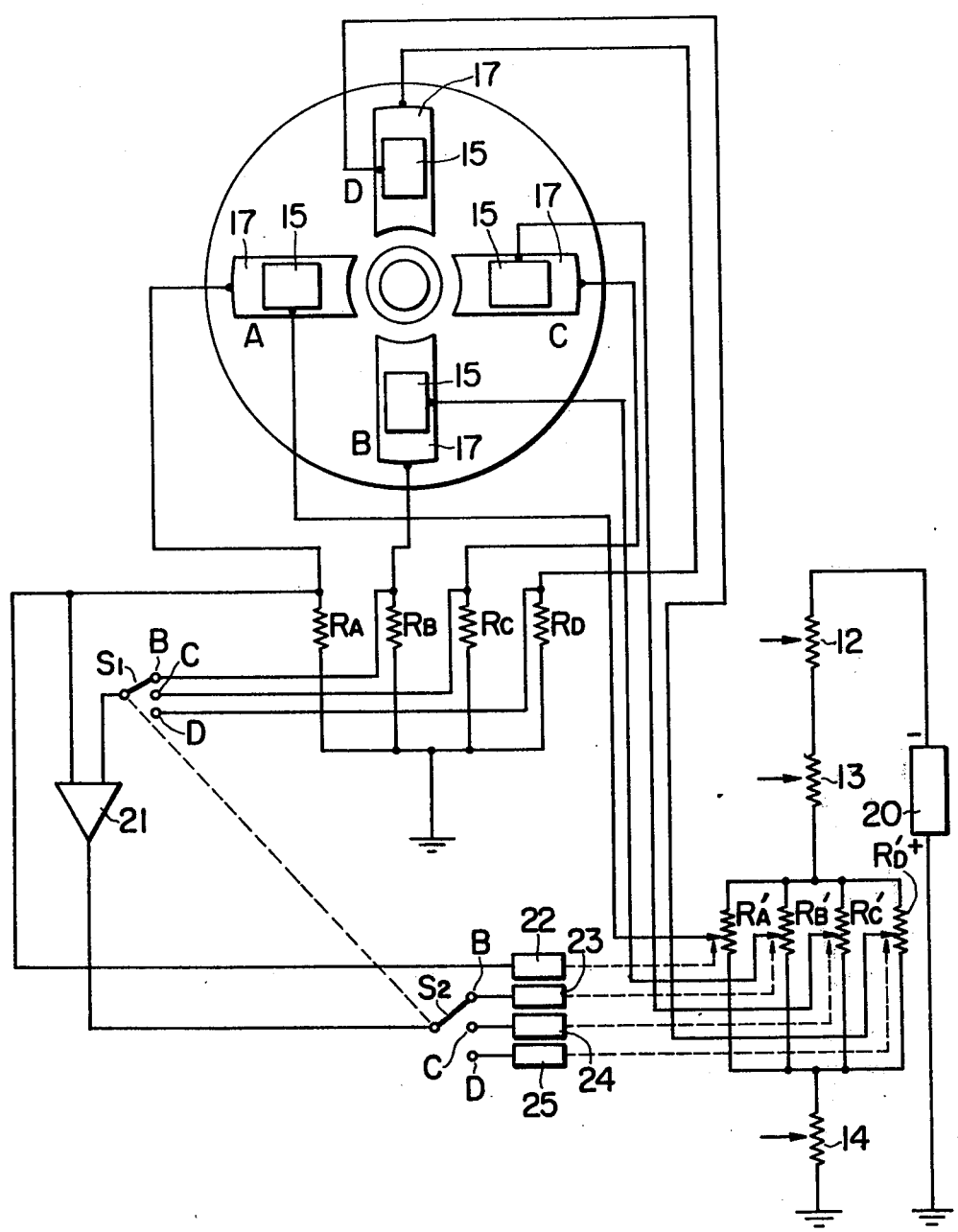
FIG. 4 is a block diagram for explaining the operation of charged-particle beam correction arrangement according to the present invention.

FIG. 4 is a block diagram for explaining the operation of an embodiment of the charged-particle beam correction arrangement wherein the detection electrodes 17 and the correction electrodes 15 are disposed in respective regions A, B, C and D. A current value detected by the detection electrode 17 of the region A is utilized as a reference value. Current values detected in the other regions B, C and D are respectively compared with the reference value in the region A. A correction is carried out so that the respective values are made equal to the reference value of the region A.

The current value to be detected from the detection electrode 17 in the region A is obtained as a voltage value across a resistance $R_A$ in FIG. 4, while the current values to be detected from the detection electrodes 17 in the regions B, C and D are respectively obtained as voltage values across resistances $R_B$, $R_C$ and $R_D$.

In order to compare with the reference value of the region A, the current value detected from the detection electrode 17 in the region B, switches $S_1$ and $S_2$ are connected to contacts B. The currents detected from the detection electrodes 17 of the regions A and B are compared in a differential amplifier 21, and the difference is delivered to a servo-amplifier 23 as an input.

The servo-amplifier 23 is driven according to the signal of the differential amplifier 21, to change the value of a resistance $R_B'$. Accordingly, a voltage to be applied to the correction electrode 15 of the region B is changed to correct the track of the charged-particle beam. The correction is stopped when the current value detected from the detection electrode 17 of the region B finally becomes equal to the current value in the region A.

Subsequently, the switches $S_1$ and $S_2$ are changed-over to terminals C and D in succession, and the same correction as provided for region B is carried out, whereby the track of the charged-particle beam is gradually corrected to come close to a true circle. In this manner, the present invention makes it possible to pass the charged-particle beam through the slit 9 under the condition that the amount of the charged particles intercepted by the slit 9 is minimized.

In performing the actual energy analysis, the voltages which are applied to the correction electrodes 15 can be superposed on the voltages which scan the deflecting electrodes 6, 7, the auxiliary electrode 8 and the cylindrical mirror type analyzer 10. Further, as the voltage to be applied to the correction electrode 15, either a positive voltage or a negative one is selected in dependence on the signal to be detected. For example, in the case of detecting an electron beam, the negative voltage is generally applied to the correction electrode 15. However, under some conditions, for example, when a fraction of the electron beam is too close to the center, the positive voltage may be applied to the correction electrode 15 so as to draw the electron beam towards the electrode.

Although the above embodiment has been explained as including four charged-particle beam correction devices disposed in four regions, the number of the devices and corresponding regions is not restricted to four but may be any number insofar as the correction devices and regions are arranged axially symmetrically. In addition, if one set of the correction devices is insufficient for the correction of the charged-particle beam, a plurality of sets may be installed.

The position of installation of the correction arrangement may be any place insofar as it lies in the vicinity of the path of the charged particles between the sample and the slit as stated previously. Preferably, however, the correction arrangement is arranged between the deflecting electrodes and the slit. Further, in the case where an auxiliary electrode 8 is provided, the correction arrangement should preferably be disposed between the auxiliary electrode and the slit.

Figure 1:
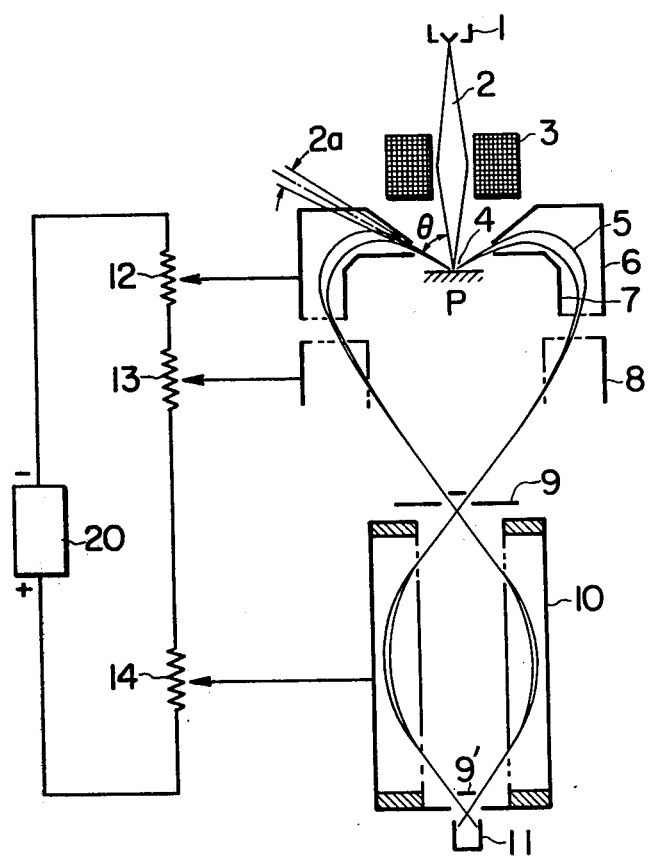
FIG. 1 schematically illustrates a prior art charged-particle analyzer.

As a prior art, charged-particle analyzer, there has also been known one in which, conversely to the case of FIG. 1, the direction of deflection by the deflecting electrodes is on the side of the electron gun 1 as viewed from the sample and the energy analyzing system is installed above the electron gun 1 as viewed in the figure. The charged-paricle beam correction means in this invention can also be installed on such type of charged-particle analyzer.

While we have shown and described several embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:

1. In a charged-particle analyzer having means for irradiating a sample with a primary bean, deflecting electrode means for focusing charged particles emitted from the sample onto a predetermined area in relation to the center axis of the primary beam., means forming a slit disposed at the focus point of the charged particles, energy analyzing means having an object point lying at the focus point, and detector means for detecting the charged particles analyzed by the energy analyzing means, the improvement comprising charged-particle beam correction means disposed axially symmetrically in the vicinity of a path of the charged particles between the sample and said slit means for correcting a deformation in the focusing of the charged particles, wherein said charged-particle beam correction means includes a plurality of detection electrodes for detecting the charged-particle beam and a plurality of correction electrodes, said detection electrodes and said correction electrodes being insulated from one another and said plurality of detection and correction electrodes being axially symmetrically disposed, respective detection electrodes detecting the charged-particle beam impinging thereon and providing an output in accordance therewith, said charged-particle beam correction means including compensating signal means for supplying a signal to respective correction electrodes so as to ensure that the charged particle beam is circular, wherein one of said detection electrodes provides a reference value output, said compensating signal means comparing the outputs from the other detection electrodes with said reference value output and providing compensating signals to the respective correction electrodes in accordance with the result of the comparison.

2. A charged-particle analyzer according to claim 1, wherein said energy analyzing means includes a cylindrical mirror type analyzer.

3. A charged-particle analyzer according to claim 1, wherein said deflecting electrode means is arranged for focusing the charged particles onto a side of said sample opposite to the side of said sample irradiated with the primary beam.

4. A charged-particle analyzer according to claim 1, further comprising insulating means affixing each detection electrode to a respective correction electrode and to said slit means.

5. A charged-particle analyzer according to claim 1, wherein said charged-particle beam correction means is disposed between said deflecting electrode means and said slit means.

6. A charged-particle analyzer according to claim 5, further comprising insulating means affixing each detection electrode to a respective correction electrode and to said slit means.

* * * * *